United States Patent

Lurie et al.

[11] Patent Number: 6,078,834
[45] Date of Patent: *Jun. 20, 2000

[54] DEVICE AND METHOD FOR DETECTION AND TREATMENT OF SYNCOPE

[75] Inventors: Keith G. Lurie, Minneapolis; David Benditt; Stanislao F. Obino, both of Edina; Paul J. Buscemi, Long Lake, all of Minn.

[73] Assignee: PharmaTarget, Inc., Minneapolis, Minn.

[*] Notice: This patent is subject to a terminal disclaimer.

[21] Appl. No.: 09/257,566

[22] Filed: Feb. 25, 1999

Related U.S. Application Data

[63] Continuation of application No. 08/831,608, Apr. 10, 1997, Pat. No. 5,919,210.

[51] Int. Cl.$^7$ .................................................. A61M 5/142
[52] U.S. Cl. ........................... 607/3; 600/513; 604/891.1
[58] Field of Search ................................ 607/3, 25, 120; 600/516, 509, 513, 515; 604/19, 890.1, 891.1

[56] References Cited

U.S. PATENT DOCUMENTS

| | | | |
|---|---|---|---|
| 3,358,690 | 12/1967 | Cohen | 128/419 |
| 3,593,718 | 7/1971 | Krasner et al. | 128/419 |
| 3,857,399 | 12/1974 | Zacouto | 128/419 |
| 4,009,721 | 3/1977 | Alcidi | 128/419 |
| 4,146,029 | 3/1979 | Ellinwood, Jr. | 128/260 |
| 4,193,393 | 3/1980 | Schlager | 128/710 |

(List continued on next page.)

OTHER PUBLICATIONS

W. Kapoor et al., "Upright Tilt Testing in Evaluating Syncope: A Comprehensive Literature Review", *The American Journal of Medicine*, vol. 97, Jul. 1994, pp. 78–88.

R. Sutton et al., "The Clinical Spectrum of Neurocardiogenic Syncope", *Journal of Cardiovascular Electrophysiology*, vol. 6, No. 7, Jul. 1995, pp. 569–576.

P. Chang–Sing et al., "Syncope: Evaluation and Management/A Review of Current Approaches to This Mulifaceted and Complex Clinical Problem", *Cardiology Clinics*, vol. 9, No. 4, Nov. 1991, pp. 641–651.

M. Gammage et al., "Initial Experience with a Rate Drop Algorithm in Malignant Vasovagal Syndrome", *European Journal of Cardiac Pacing and Electrophysiology*, vol. 5, No. 1, 1995, 5 pages.

S. Jasbir et al., Cardiac Pacing During Neurocardiogenic (Vasovagal) Syncope, *Journal of Cardiovascular Electrophysiology*, vol. 6, No. 9, Sep. 1995, pp. 751–760.

T. Kus et al., "Vasovagal Syncope: Management with Atrioventricular Sequential Pacing and Beta–Blockade", *The Canadian Journal of Cardiology*, vol. 5, No. 8, Nov./Dec. 1989, 5 pages.

D. Benditt et al., "Cardiac Pacing for Prevention of Recurrent Vasovagal Syncope", *Annals of Internal Medicine*, vol. 122, No. 33, Feb. 1995, pp. 204–209.

Lurie et al., "Syncope and the Autonomic Nervous System", *Journal of Cardiovascular Electrophysiology*, vol. 7, No. 8, Aug. 1996, pp. 760–776.

*Primary Examiner*—Kennedy J. Schaetzle
*Attorney, Agent, or Firm*—Crompton, Seager & Tufte, LLC

[57] ABSTRACT

The invention disclosed herein relates to an implantable medical device for detection and treatment of syncope comprising an algorithm for determining the presence of syncope based on physiological activity associated with the onset of a syncopal episode, and a means for infusion a drug. Drug infusion therapy may be used along or in combination with pacing. The physiological activities detected and used by the device are selected from the group including changes in heart rate, heart rate variability, QT interval, PR interval, pressure, blood flow, vagal nerve activity, temperature, pH, and AV conduction times, respiration rate, position, motion, and combinations thereof. Drugs which may be used with the invention include pharmaceutical compositions which are capable of both endocardial administration and treatment of syncope, such as compositions comprising beta-blockers.

1 Claim, 6 Drawing Sheets

U.S. PATENT DOCUMENTS

| | | | |
|---|---|---|---|
| 4,202,339 | 5/1980 | Wirtzfeld et al. | 128/419 |
| 4,228,803 | 10/1980 | Rickards | 128/419 |
| 4,252,124 | 2/1981 | Maurer et al. | 128/635 |
| 4,312,355 | 1/1982 | Funke | 128/419 |
| 4,313,442 | 2/1982 | Knudson et al. | 128/419 |
| 4,428,378 | 1/1984 | Anderson et al. | 128/419 |
| 4,566,456 | 1/1986 | Koning et al. | 128/419 |
| 4,730,619 | 3/1988 | Koning et al. | 128/419 |
| 4,791,931 | 12/1988 | Slate | 128/419 |
| 4,960,129 | 10/1990 | dePaola et al. | 128/695 |
| 5,040,533 | 8/1991 | Fearnot | 128/419 |
| 5,065,759 | 11/1991 | Begemann et al. | 128/419 |
| 5,113,859 | 5/1992 | Funke | 128/419 |
| 5,213,098 | 5/1993 | Bennett et al. | 128/419 |
| 5,233,984 | 8/1993 | Thompson | 607/18 |
| 5,330,505 | 7/1994 | Cohen | 607/6 |
| 5,342,404 | 8/1994 | Alt et al. | 607/6 |
| 5,441,525 | 8/1995 | Shelton et al. | 607/23 |
| 5,464,434 | 11/1995 | Alt | 607/6 |
| 5,501,701 | 3/1996 | Markowitz et al. | 607/9 |
| 5,514,163 | 5/1996 | Markowitz et al. | 607/9 |
| 5,527,344 | 6/1996 | Arzbaecher et al. | 607/3 |
| 5,540,728 | 7/1996 | Shelton et al. | 607/23 |
| 5,560,368 | 10/1996 | Berger | 128/703 |
| 5,676,686 | 10/1997 | Jensen et al. | 607/9 |
| 5,693,028 | 12/1997 | Shillington | 604/240 |

SENSORS

1. Heart Rate (R-R interval)
2. Atrioventricular interval (AVI)
3. QT interval (QT)
4. QT/R-R ratio
5. Heart Rate Variability indices (HF,LF,LF/HF ratio)
6. QRS or Ventricular Electrogram integral (area under depolarization signal)
7. QRS duration
8. Myocardial contractility index (accelerometer signal) (KL ± this item as it is part of the lead idea to be written up)
9. Subcutaneous blood flow, mean value (SubQ BF)
10. SubQ BF variability indices

*Fig. 4*

EXTENDED PRE-SYNCOPAL PHASE

1. R-R < baseline but >500ms
2. AVI < or = baseline
3. QT < baseline, and relatively constant (i.e. ± x, where x=25-40 ms, or 5% of current value)
4. QT/R-R ratio fixed (±5%) or decreasing from baseline value
5. HRV - not critical at this stage, but LF/HF ratio > or = baseline
6. QRS integral < or = baseline
7. QRS duration < or = baseline
8. Contractibility index (magnitude of accelerometer signal) > baseline
9. SubQ BF-not critical at this stage, but mean value = or > baseline
10. SubQ BF variability, LF/HF ratio = or > baseline

*Fig. 5*

IMMEDIATE PRE-SYNCOPAL PHASE

1. R-R < baseline but >500 ms, Trend to longer R-R value
2. AVI < or = baseline
3. QT < baseline, and relatively constant (i.e. ± x, where x=25-40 ms, or 5% of current value)
4. QT/R-R ratio fixed (±5%) or decreasing from baseline value
5. HRV - LF/HF ratio > or = baseline; trend to lower values
6. QRS integral < or = baseline
7. QRS duration < or = baseline
8. Contractibility index (magnitude of accelerometer signal) > baseline
9. SubQ BF- mean value = or > baseline
10. SubQ BF variability, LF/HF ratio = or > baseline, trend to decreasing LF/HF ratio

*Fig. 6*

SYNCOPE ONSET

1. R-R < baseline but >500 ms, Trend to longer R-R value
2. AVI < or = baseline
3. QT < baseline, and relatively constant (i.e ± x, where x=25-40 ms, or 5% of current value
4. QT/R-R ratio fixed (±5%) or decreasing from immediate presyncope value
5. HRV - LF/HF ratio < baseline
6. QRS integral < or = baseline
7. QRS duration < or = baseline
8. Contractibility index (magnitude of accelerometer signal) > baseline
9. SubQ BF, mean value = or > baseline
10. SubQ BF variability, LF/HF ratio < immediate presyncope value, trend to decreasing LF/HF ratio

DEVICE AND METHOD FOR DETECTION AND TREATMENT OF SYNCOPE

This application is a continuation of application Ser. No. 08/831,608, filed Apr. 10, 1997, now U.S. Pat. No. 5,919,210.

FIELD OF THE INVENTION

The invention relates to the field of implantable medical devices. In particular, the invention relates to an implantable device which detects syncope, such as vasovagal syncope, and administers treatment in response thereto by endocardial drug infusion alone or in combination with pacing.

BACKGROUND OF THE INVENTION

Vasovagal syncope, or neutrally-mediated syncope, is a complex fainting disorder which affects a significant number of people. The degree to which individuals are affected by vasovagal syncope varies, and some individuals experience multiple episodes of vasovagal syncope. Accordingly, more aggressive treatments are required for such individuals.

Several treatments for vasovagal syncope are known in the art. For example, oral pharmacological therapies, such as administration of beta-blockers, have been used. However, oral therapy alone is inadequate to prevent sudden episodes of vasovagal syncope. Further, the therapeutic efficacy of such treatments remains unclear, as it is difficult to assess efficacy of such treatments in randomized trials.

Another proposed treatment for vasovagal syncope is pacemaker therapy alone. For example, see Markowitz et al., U.S. Pat. No. 5,501,701, which teach detection and treatment of vasovagal syncope using a device comprising a pacemaker and means for detecting syncopal episodes based on decreased heart rate.

Pacing therapies used in conjunction with various sensors of physiological parameters are well known in the art. A pacemaker using P-wave sensors is taught by Knudson et al., U.S. Pat. No. 4,313,442. A pacemaker responsive to changes in Q-T interval is taught in Rickards, U.S. Pat. No. 4,228,803. Sensed atrial and ventricular signals are used in the pacing device of Funke, U.S. Pat. No. 4,312,355. Alcidid, U.S. Pat. No. 4,009,721 teaches a pacemaker controlled by blood pH. A pacemaker which uses sensed molecular blood oxygen levels is taught by Wirtzfeld et al., U.S. Pat. No. 4,202,339. A pacemaker which uses sensed respiratory rates is taught by Krasner, U.S. Pat. No. 3,593,718. Pacer systems based on motion sensors are taught by Anderson et al., U.S. Pat. No. 4,428,378. Cohen, U.S. Pat. No. 3,358,690 and Zacouto, U.S. Pat. No. 3,857,399 teach pacing responsive to sensed cardiac pressure.

However, pacemaker therapy alone has been found to lack efficacy in many patients suffering from vasovagal syncope. Combination therapy, such as atrioventricular pacing with intravenous administration of beta-blockers, is also known. Given the sudden and intermittent occurrence of syncopal episodes, however, normal intravenous routes of drug infusion are often not available at the occurrence of such events and therefor too late to be of practical use.

Hence, there still exists a need for an improved method of treating dysautonomic syncope which is capable of accurately detecting the onset of the syncopal episode and administers treatment in accurate and efficient manner to prevent the occurrence thereof.

SUMMARY OF THE INVENTION

The invention provides an implantable device for detection and treatment of dysautonomic syncopes such as vasovagal syncope comprising an algorithm which accurately detects the onset of syncope using sensed physiological activities associated therewith and endocardially infuses a drug in response thereto. In accordance with the present invention, a method is provided for treating syncope using such a device and detection algorithm. Generally, the implantable device comprises sensors, a drug infusion catheter, and a microprocessing unit and detection algorithm.

The sensing leads are placed in locations where the physiological activity to be detected is most prominent and more feasibly detected. A variety of sensors known in the art may be used to detect the onset of a syncopal episode. The combination of sensors used in the device will depend upon the physiological activities to be used for the detection of syncope. Such sensors include, but are not limited to, those which can detect heart rate (R—R interval), atrioventricular interval (AVI), QT interval, QT/R—R ratio, heart rate variability indices such as HF, LF, LF/HF ratio, QRS or ventricular electrogram integral (area under depolarization signal), QRS duration, myocardial contractility index (accelerometer signal), subcutaneous blood flow mean value (SubQ BF), SubQ BF variability indices, motion, pH, temperature, position and chest wall impedance for monitoring respiration rate.

The algorithm used in conjunction with the device determines the need for treatment based on sensed physiological activities associated with the onset of syncope. The physiological activities used to determine the need for treatment include changes in heart rate, heart rate variability, QT interval, PR interval, pressure, blood flow, vagal nerve activity, temperature, pH, and AV conduction times, position, respiration rate and combinations thereof. The algorithm detection parameters will correspond to the sensors used in the device and the detected physiological activity. The detection algorithm operates in three primary time frames relating to syncope episodes: extended pre-syncopal phase, immediate pre-syncopal phase, and syncope onset.

The physiological activity sensors and physiological parameters to be used in conjunction with the detection algorithm are preprogrammed according to the patient's symptoms and needs. The values to be used in the device to declare the onset of vasovagal syncope may be programmed externally using a telemetry interface known in the art.

The drug infusion catheter is placed according to the desired treatment regimen. For example, the drug infusion catheter may be placed within the coronary sinus, right atrium or right ventricle to provide rapid infusion with little dilution of pharmacological therapy.

Suitable drugs for use with the invention include pharmaceutical compositions capable of endocardial administration and able to treat vasovagal syncope. Examples of such drugs include, but are not limited to, pharmaceutical compositions comprising beta-adrenergic blocking agents, protain emide, type 1 antiarrhythmic agents such as disopyramide, class II agents such as propafenone, alphaagonists such as ephedrine and midodrine, and other antiarrhymic agents such as amiodarone, and combinations thereof.

A pacemaker may be incorporated into the device and used in conjunction with drug infusion treatment. When drug infusion therapy is used in combination with a pacemaker, the pacing treatment may be reserved until a predetermined threshold level value of tolerable bradycardia is exceeded, abnormally low value of the QT/R—R ratio is detected, or decrease in heart rate is anticipated based upon continuously monitored physiologic parameters as described above. Electrical stimulation occurs in addition to drug infusion only upon the detection of significant bradycardia or the low QT/R—R value. The pacemaker used in accordance with the invention is preferably a dual chamber pacemaker.

The device and method of the present invention accurately detects the onset of vasovagal syncope and provides a less painful and more efficacious infusion treatment therefore. The device and method of the present invention can be programmed externally by the patient so as to operate according to the patient's particular condition and needs. Further, different combinations of sensed changes in physiological activity may be used to determined the need for treatment.

BRIEF DESCRIPTION OF THE DRAWINGS

The following descriptions, when taken together with the accompanying drawings and numerical designations which remain consistent throughout, illustrate the objects and advantages of the invention disclosed therein.

DETAILED DESCRIPTION OF THE INVENTION

Figure 1:
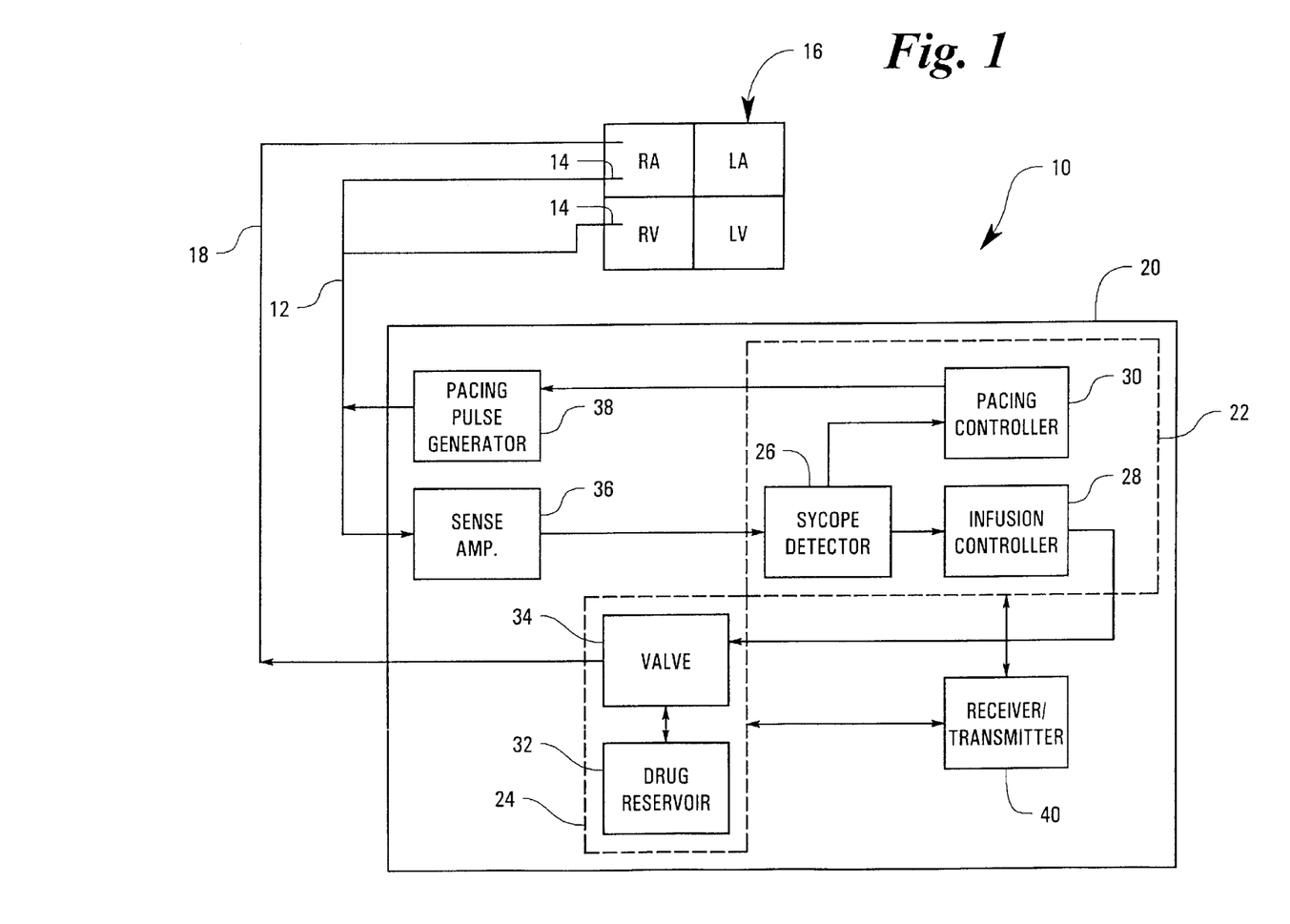
FIG. 1 illustrates a block diagram of a device using combined therapy features of both a drug infusion and pacing apparatus in accordance with the present invention.

The block diagram of FIG. 1 shows a device 10 in accordance with the present invention. Device 10 includes one or more leads 12 which can include a plurality of electrodes 14 for pacing the right atrium (RA), left ventricle (LV) and/or right ventricle (RV) of heart 16. Lead 12 can include a plurality of sensors attached to heart 16 for measuring any of various physiological parameters as described more particular with respect to FIG. 3 below. Device 10 also includes a drug infusion catheter 18 which here is shown schematically, and apart from lead 12. Lead 12 and conduit 18 may be combined into a single catheter. Preferably conduit 18 extends into the right atrium.

Device 10 includes a hermetically sealed, implantable container 20, including a microprocessor 22 and drug pump 24. Microprocessor 22 includes a vasovagal syncope (VS) detector 26 and infusion controller 28 and a pacing controller 30. Drug pump 24 includes a drug reservoir 32 and a valve 34 such as a solenoid valve. Drug infusion devices suitable for use with the invention include any device which is capable of delivering drugs directly into the chambers or blood vessels of the heart in response to instructions from a remote source. For example, an endocardial drug infusion apparatus such as that found in Cammilli et al., U.S. Pat. No. 5,220,917, incorporated herein by reference, may be used.

Device 10 also includes a sense amplifier 36 and a pacing pulse generator 38. Sense amplifier 36 receives signals through lead 12 from various sensors connected to heart 16 to sense the parameters described below in more detail with respect to FIG. 3. A dual chamber pacemaker is preferred. The pacing leads are located according the desired electrical stimulating regimen, for example, right atrium or right ventricle. One skilled in the art, would be aware of the various sensors available to detect these parameters and the advisability of providing additional sensing amplifiers as necessary for these detectors.

Device 10 also includes a receiver/transmitter 40 which can be accessed non-invasively from exterior the patient. Receiver/transmitter 40 can be used to program microprocessor 22 including writing to memory in microprocessor 22 various 25 baseline values of the parameters of FIG. 3 below for use in an algorithm described in more detail below. Data from the microprocessor and/or drug pump can be transmitted from device 10 to an external device for monitoring.

The various components shown in FIG. 1 are well known to those skilled in the art. This is particular true with respect to the pacing art. The combination of these various components, however, is made in accordance with applicant's invention.

Figure 3:
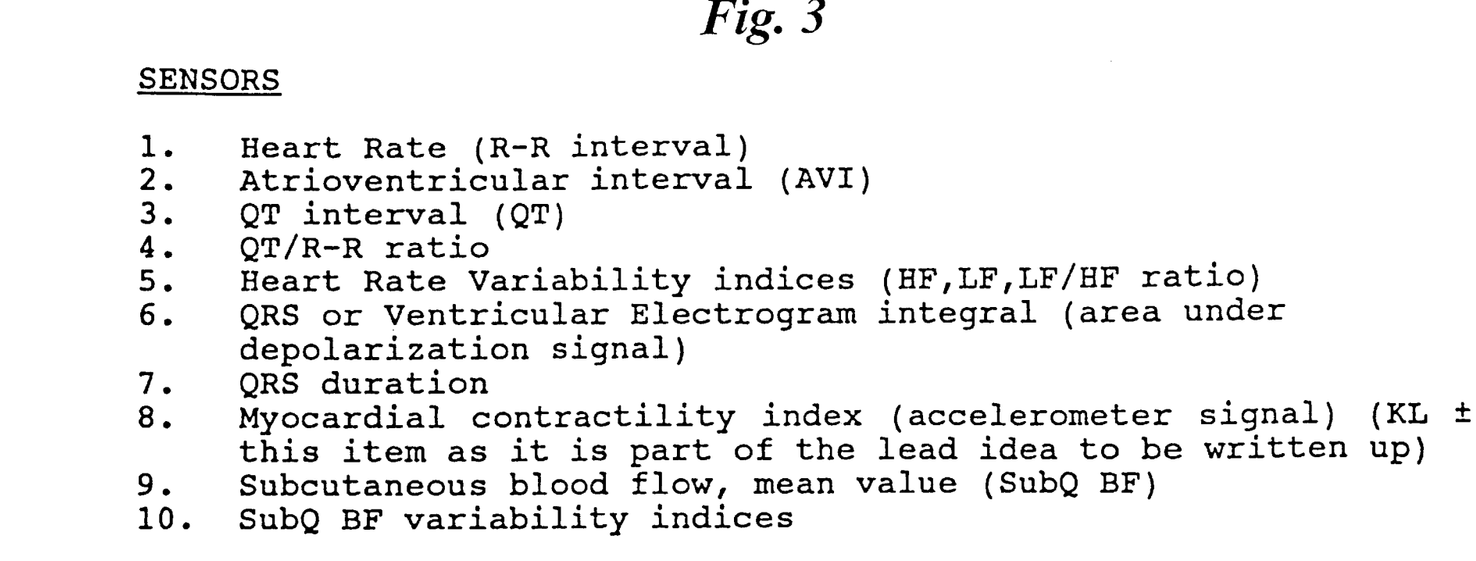
FIG. 3 is a table of physiologic parameters which can be used to detect vasovagal syncope.

In use, a baseline of the parameters of FIG. 3 are stored in microprocessor 22. The base line parameters may be pre-programmed into microprocessor 22, programmed by way of receiver/transmitter 40 or generated by direct heart monitoring through lead 12. The various parameters shown in FIG. 3 are monitored by syncope detector 26 by way of the sensors connected to heart 16, lead 12 and sense amplifier 36. These values are compared to the baseline values in accordance with the algorithms described in more detail below. In a preferred embodiment, the baseline values are calculated as a moving average of the "current" value from each sensor over a period of about 1 to 10 minutes. The "current" values can be collected at an interval of, for example, about 5 seconds.

In accordance with the algorithm infusion of drugs consistent with the protocol described below may be initiated by infusing controller 28 which signals pump 24 to open valve 34 and discharge drugs from drug reservoir 32 into the right atrium of heart 16 by way of catheter 18. If drug infusion is insufficient to control the vasovagal syncope, pacing controller 30 will signal pacing pulse generator 38 to pace heart 16.

Sensing leads 12 are preferably placed in locations where the physiological activity associated with the onset of vasovagal syncope is most prominent and more feasibly detectable. Drug infusion catheter 18 is located within a chamber of the heart, or coronary sinus.

Suitable drugs for use with the invention include pharmaceutical compositions capable of endocardial administration and which treat vasovagal syncope. Examples of such drugs include, but are not limited to, beta-adrenergic blocking agents, alpha-agonists such as ephedrine and midodrine, and combinations thereof. The pharmaceutical composition comprises a drug for treating vasovagal syncope in conjunction with a pharmaceutically acceptable carrier or adjuvant.

Administration of the pharmaceutical composition occurs over a time period ranging from approximately 10 seconds to 24 hours, depending upon the desired treatment regimen and pharmaceutical composition. The composition is administered in concentrations sufficient to treat the symptoms associated with the onset of syncopal episodes.

Choice of pharmaceutical agent, dosages, concentrations and formulations will vary according to the desired treatment regimen and the patient's particular needs and is within the level of ordinary skill in the art.

Figure 2:
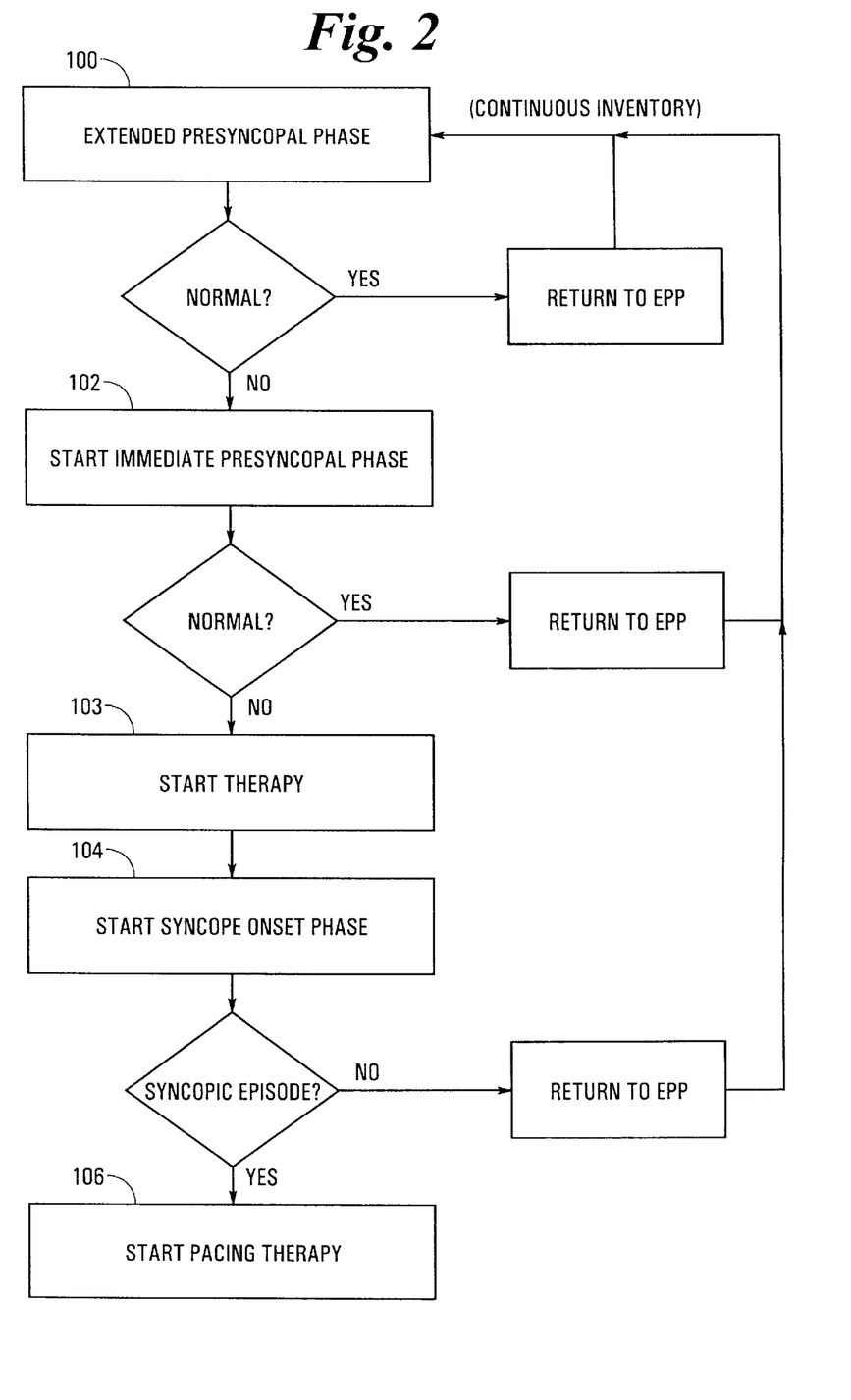
FIG. 2 illustrates a flow diagram of the algorithm for determining the need for treatment in accordance with the present invention.

One embodiment of the detection algorithm is shown in FIG. 2. Generally, the detection algorithm operates in three primary time frames relating to vasovagal syncope episode: extended pre-syncopal phase, immediate pre-syncopal phase, and syncope onset. For illustrative purposes, FIG. 3 is a table of parameters associated with vasovagal syncope which can be monitored during each phase, these include: R—R interval, AVI, QT, QT/R—R ratio, HRV-LF/HF ratio, QRS integral, QRS duration, contractibility index, SubQ BF mean value, SubQ BF variability. Respiration rate, motion and position can also be monitored.

The device 10 used in accordance with the invention can be programmed externally by the patient so as to adjust the detection to better operate in cooperation with the patient's particular condition. Hence, different combinations of sensors corresponding to changes in physiological activity may be used to determine the need for treatment.

Generally, predetermined baseline values for normal physiological parameters are programmed into the device and can be modified according to a particular patient's needs or a moving average of "current" values can be calculated as described above. During the extended pre-syncopal phase of the detection algorithm, the immediate pre-syncopal phase, and the syncope onset phase, the desired physiological activities are sensed and are sampled for their current value periodically, for example, every 5 seconds or continuously. The current values for each sensed activity are evaluated against a background of corresponding baseline values or, for example, a rolling average over the preceding 5 to 10 minutes. An evaluation of normality is made for each sensed activity based on the comparison between actual current and baseline values. When the pre-selected combination of abnormal results occur, the subsequent phase of therapy is initiated.

The algorithm operates by maintaining a continuous inventory of current values corresponding to each sensed activity. The current values are measured against predetermined baseline values recorded in memory. Generally, the differences in current values and baseline values are used by the algorithm to determine the need for treatment.

Figure 4:
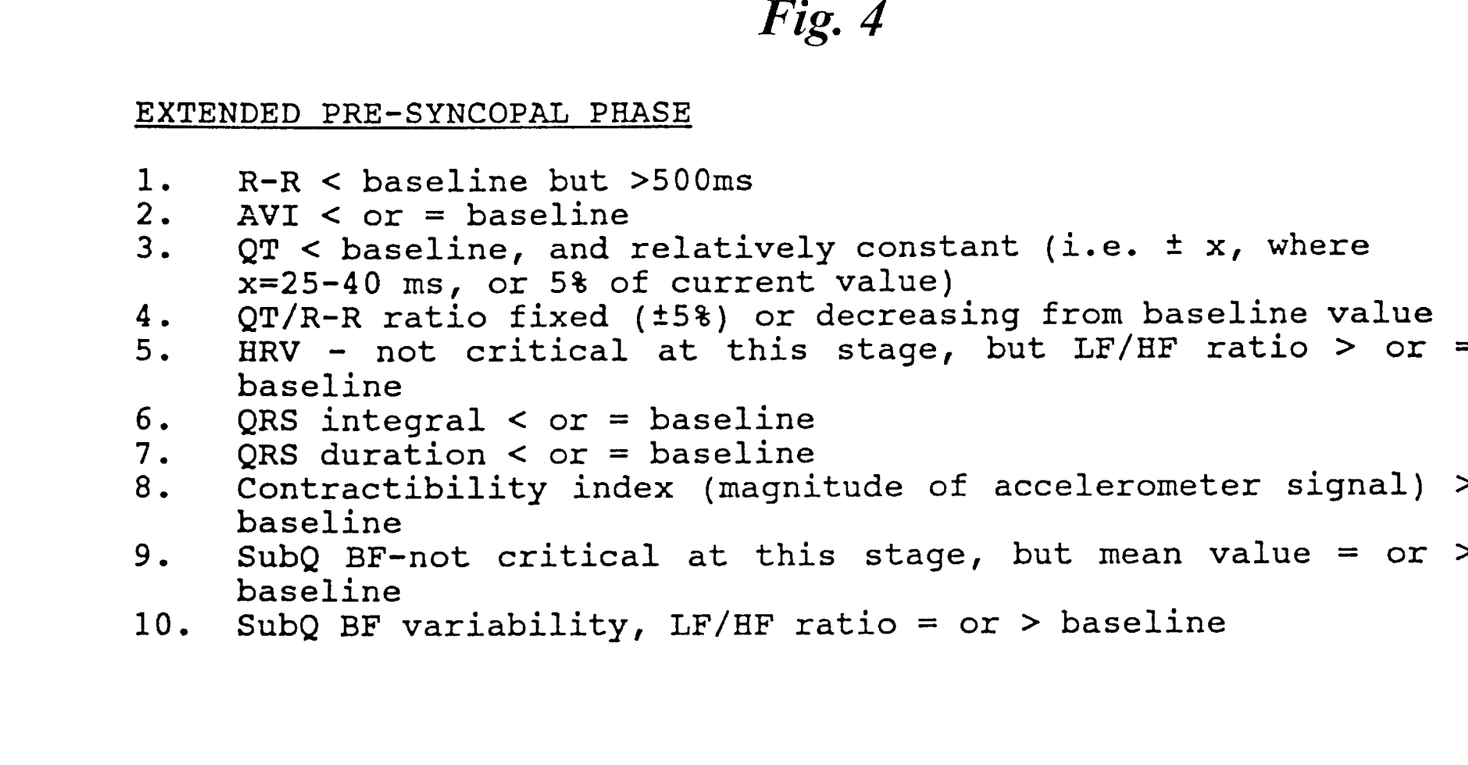
FIG. 4 is a table of the values of the parameters of FIG. 3 corresponding to an abnormal condition during the extended presyncopal phase of the algorithm.

With the continuous inventory of current values, the algorithm periodically compares the baseline value of selected ones of the parameters of FIG. 3 to the values given in FIG. 4 to determine if an extended pre-syncopal phase 100 has commenced. Such a pre-syncopal phase 100 generally operates approximately 1 to 2 minutes prior to a syncopal episode. The pre-syncopal phase will be considered to have commenced if the parameters of FIG. 3 have the general values given in FIG. 4. However, for each patient, the parameters to be monitored can be a subset of those described herein. Those parameters selected correspond to the symptoms of the particular patients.

Figure 5:
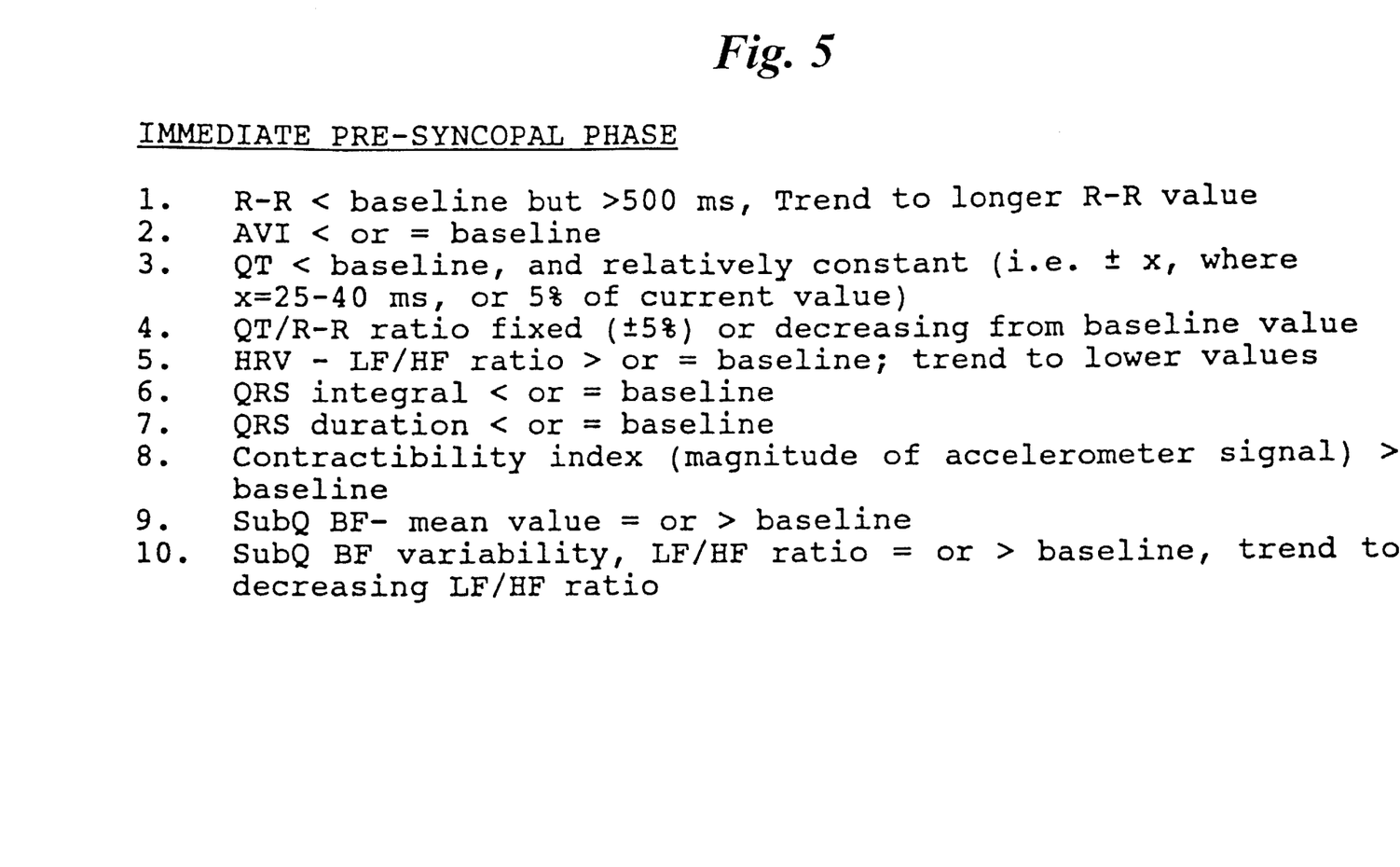
FIG. 5 is a table of the values of the parameters of FIG. 3 corresponding to an abnormal condition during the immediate presyncopal phase of the algorithm.

If it has been determined that the pre-syncopal phase has indeed commenced, then monitoring continues and comparison of current values of the selected ones of the parameters of FIG. 3 is made to the values given in FIG. 5 to determine if the immediate pre-syncopal phase 102 has begun. The immediate pre-syncopal phase 102 operates approximately 3 to 60 seconds prior to the onset of syncope. If it is determined that the immediate pre-syncopal phase 102 has begun, the drug treatment protocol is activated at 103.

Figure 6:
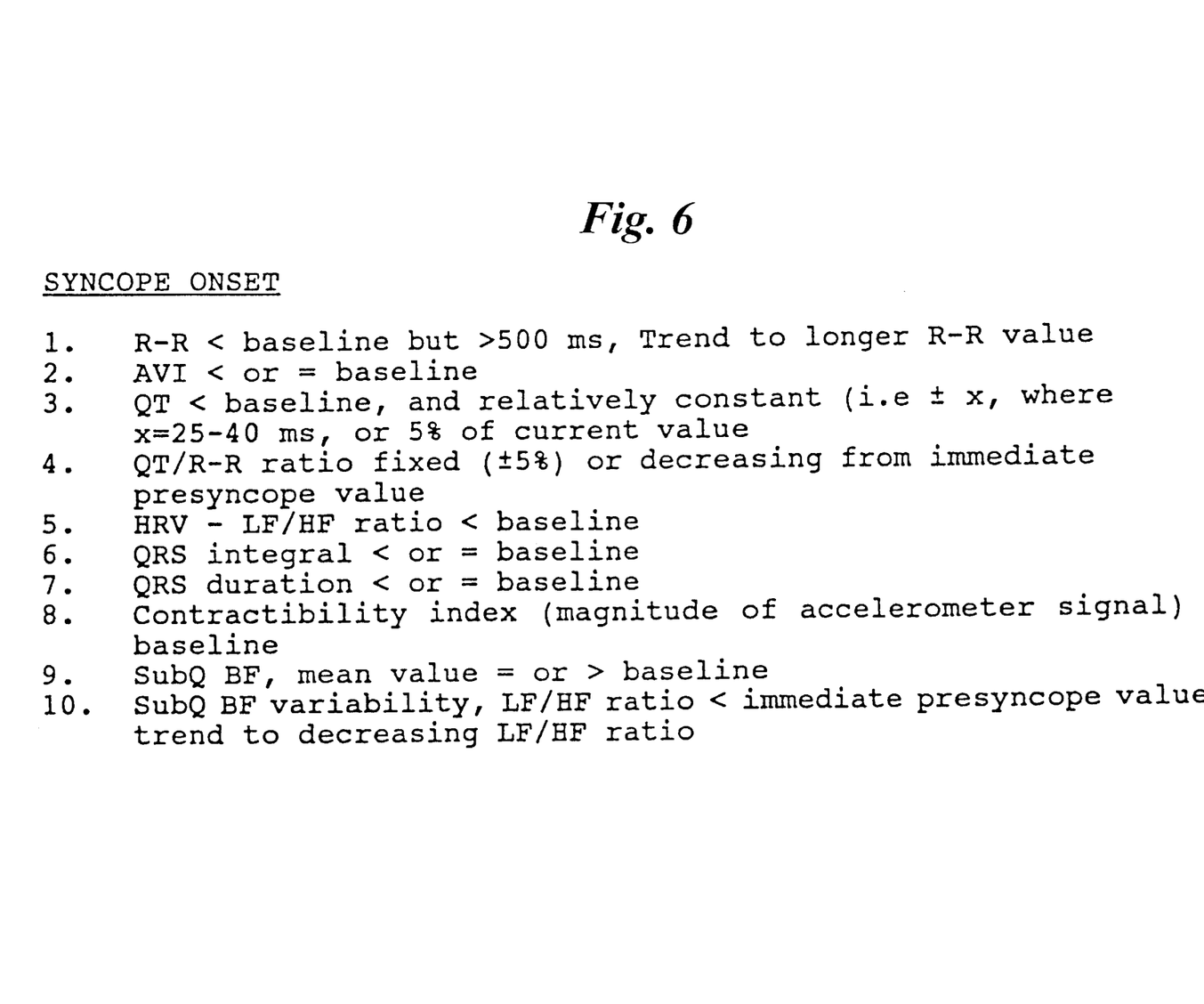
FIG. 6 is a table of the parameter values of the parameters of FIG. 3 corresponding to an abnormal condition during the syncope onset phase of the algorithm.

Following the detection of the immediate pre-syncopal phase 102, the algorithm tests at 104 for the onset of vasovagal syncope, about 3 to 60 seconds following the pre-syncopal phase, by comparing current values of selected ones of the parameters of FIG. 3 to those in FIG. 6. If those in FIG. 6 are present, vasovagal syncope has begun. Pacing therapy is then used in addition to endocardial drug infusion. In alternate embodiments of the invention, pacing may commence at the time drug infusion begins or can precede drug infusion.

It should be noted that in determining the onset of syncope, the algorithm may depart from that described above in that the current QT/R—R ratio may be compared with the current value detected in the immediate pre-syncopal phase, or the immediate pre-syncopal phase and the last value determined in extended pre-syncopal phase. This would indicate a continuing decline in the QT/R—R ratio.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for detection and endocardial treatment of syncope in a patient in need of treatment thereof, comprising the steps of:

sensing physiological activity associated with the onset of syncope;

determining the presence of an onset of syncope; and infusing a therapeutically effective amount of a pharmaceutical composition for treating syncope directly into the heart in response to said determination, wherein the pharmaceutical composition is selected from the group consisting of beta-adrenergic blocking agents, protain emide, disopyramide, propafenone, ephedrine, midodrine, amiodarone and combinations thereof.

* * * * *